United States Patent
Qiao et al.

(10) Patent No.: US 6,916,620 B2
(45) Date of Patent: *Jul. 12, 2005

(54) RANDOM ARRAY OF MICRO-SPHERES FOR THE ANALYSIS OF NUCLEIC ACID USING ENZYME DIGESTION

(75) Inventors: Tiecheng A. Qiao, Webster, NY (US); Krishnan Chari, Fairport, NY (US); Douglas L. Vizard, Durham, CT (US)

(73) Assignee: Eastman Kodak Company, Rochester, NY (US)

( * ) Notice: Subject to any disclaimer, the term of this patent is extended or adjusted under 35 U.S.C. 154(b) by 42 days.

This patent is subject to a terminal disclaimer.

(21) Appl. No.: 10/098,642
(22) Filed: Mar. 15, 2002

(65) Prior Publication Data
US 2003/0175719 A1 Sep. 18, 2003

(51) Int. Cl.[7] .............................. C12Q 1/68; C12M 1/36; C12N 11/16; G01N 15/06; C07H 21/04
(52) U.S. Cl. ............................ 435/6; 435/7.1; 435/174; 435/283.1; 435/287.2; 435/287.99; 435/288.7; 422/68.1; 422/82.05; 436/23.1; 436/24.3
(58) Field of Search ......................... 435/6, 7.1, 174, 435/283.1, 287.2, 287.9, 288.7; 422/68.1, 82.05; 536/23.1, 24.3

(56) References Cited
U.S. PATENT DOCUMENTS

| 4,873,102 A | * 10/1989 | Chang et al. ............... 427/130 |
| 5,412,087 A | 5/1995 | McGall et al. |
| 5,489,678 A | 2/1996 | Fodor et al. |
| 5,981,180 A | 11/1999 | Chandler et al. |
| 6,023,540 A | 2/2000 | Walt et al. |
| 6,094,966 A | 8/2000 | Papen et al. |
| 6,146,899 A | * 11/2000 | Porter et al. .................. 436/94 |
| 6,266,459 B1 | 7/2001 | Walt et al. |
| 2002/0172716 A1 | * 11/2002 | Walt et al. .................. 424/491 |
| 2003/0138842 A1 | * 7/2003 | Seul et al. ................... 435/7.1 |

FOREIGN PATENT DOCUMENTS

WO    WO 00/16101    * 3/2000

OTHER PUBLICATIONS

Jane Ferguson, Frank Steemers, David Walt, "High–Density Fiber–Optic DNA Random Microsphere Array", Anal. Chem. 2000, vol. 72, pp. 5618–5624.
Science, 251, pp. 767–773, 1991.

(Continued)

Primary Examiner—BJ Forman
(74) Attorney, Agent, or Firm—Kathleen Neuner Manne (57) ABSTRACT

A method of identifying nucleic acid samples comprising: providing a mircoarray including a substrate coated with a composition including a population of nucleic acid probe modified micro-spheres immobilized in a coating containing a gelling agent or a precursor to a gelling agent, wherein a first portion of the micro-spheres is submerged in the gelatin coating and a second portion is exposed above the gelatin coating and is substantially free of gelatin, at least one sub-population of the population micro-spheres containing an optical barcode generated from at least one colorant associated with the micro-spheres and including a nucleic acid probe sequence; contacting the array with a target nucleic acid sequence; and detecting the color barcode of the sub-population of micro-spheres due to the interaction of the probe nucleic acid sequence and the fluorescently/chemiluminescently labeled nucleic acid sample target nucleic acid sequence.

25 Claims, 7 Drawing Sheets

OTHER PUBLICATIONS

Nature Biotech, vol. 19, pp. 631–635, 2001.

P.I. Rose, Theory of the Photgraphic Process, 4th edition, T.H. James ed., pp. 51–67.

Secundrum Artem, vol. 4, No. 5, Lloyd V. Allen, no date provided.

Edward Cohen and Edgar B. Gutoff, Chapter 1, Modern Coating and Drying Technology, Interfacial Engineering Series, vol. 1, 1992, VCH Publishers Inc., New York, NY.

I. Piirma, Emulsion Polymerization, Academic Press, New York, NY, 1982–table of contents only.

T.H. Whitesides and D.S. Ross, J. Colloid Interface Science, vol. 169, pp. 48–59, 1985.

TechNote #205, Covalent Coupling, Bangs Laboratories, Inc., #002, 1999.

* cited by examiner

RANDOM ARRAY OF MICRO-SPHERES FOR THE ANALYSIS OF NUCLEIC ACID USING ENZYME DIGESTION

FIELD OF THE INVENTION

This invention concerns biological microarray technology in general. In particular, it concerns a nucleic acid microarray system comprising random distributed nucleic acid probe modified micro-spheres coated on a substrate that contained no designated sites prior to coating. The micro-spheres contain optical barcodes generated from one or more colorants associated with the micro-spheres.

BACKGROUND OF THE INVENTION

Ever since it was invented in the early 1990s (Science, 251, 767–773, 1991), high-density arrays formed by spatially addressable synthesis of bioactive probes on a 2-dimensional solid support has greatly enhanced and simplified the process of biological research and development. The key to current microarray technology is deposition of a bioactive agent at a single spot on a microchip in a "spatially addressable" manner.

Current technologies have used various approaches to fabricate microarrays. For example, U.S. Pat. Nos. 5,412,087, and 5,489,678 demonstrate the use of a photolithographic process for making peptide and DNA microarrays. The patent teaches the use of photolabile protecting groups to prepare peptide and DNA microarrays through successive cycles of deprotecting a defined spot on a 1 cm×1 cm chip by photolithography, then flooding the entire surface with an activated amino acid or DNA base. Repetition of this process allows construction of a peptide or DNA microarray with thousands of arbitrarily different peptides or oligonucleotide sequences at different spots on the array. This method is expensive. An ink jet approach is being used by others (e.g., U.S. Pat. Nos. 6,079,283; 6,083,762; and 6,094,966) to fabricate spatially addressable arrays, but this technique also suffers from high manufacturing cost in addition to the relatively large spot size of 40 to 100 μm. Because the number of bioactive probes to be placed on a single chip usually runs anywhere from 1000 to 100000 probes, the spatial addressing method is intrinsically expensive regardless how the chip is manufactured. An alternative approach to the spatially addressable method is the concept of using fluorescent dye-incorporated polymeric beads to produce biological multiplexed arrays. U.S. Pat. No. 5,981,180 discloses a method of using color coded beads in conjunction with flow cytometry to perform multiplexed biological assay. Micro-spheres conjugated with DNA or monoclonal antibody probes on their surfaces were dyed internally with various ratios of two distinct fluorescence dyes. Hundreds of "spectrally addressed" micro-spheres were allowed to react with a biological sample and the "liquid array" was analyzed by passing a single micro-sphere through a flow cytometry cell to decode sample information. U.S. Pat. No. 6,023,540 and 6,266,459 discloses the use of fiber-optic bundles with pre-etched microwells at distal ends to assemble dye loaded micro-spheres. The surface of each spectrally addressed micro-sphere was attached with a unique bioactive agent and thousands of micro-spheres carrying different bioactive probes combined to form "beads array" on pre-etched microwells of fiber optical bundles. More recently, a novel optically encoded micro-sphere approach was accomplished by using different sized zinc sulfide-capped cadmium selenide nanocrystals incorporated into micro-spheres (Nature Biotech. 19, 631–635, 2001). Given the narrow band width demonstrated by these nanocrystals, this approach significantly expands the spectral bar coding capacity in micro-spheres.

Even though the "spectrally addressed micro-sphere" approach does provide an advantage in terms of its simplicity over the old fashioned "spatially addressable" approach in microarray making, there was still needs in the art to make the manufacture of biological microarrays less difficult and less expensive and to provide nucleic acid identification systems that are accurate, less complex and less expensive.

U.S. Ser. No. 09/942,241 provides a microarray that is less costly and easier to prepare than those previously disclosed because the support need not be modified; nevertheless the micro-spheres remain immobilized on the substrate.

U.S. Ser. No. 09/942, 241 provides a microarray comprising: a substrate coated with a composition comprising micro-spheres dispersed in a fluid containing a gelling agent or a precursor to a gelling agent, wherein the micro-spheres are immobilized at random positions on the substrate. The substrate is free of receptors designed to physically or chemically interact with the micro-spheres. That invention utilizes a unique coating composition and technology to prepare a microarray on a substrate that need not be pre-etched with microwells or pre-marked in any way with sites to attract the micro-spheres, as disclosed in the art.

U.S. Ser. No. 09/942,241 teaches various coating methods but exemplifies machine coating, whereby a support is coated with a fluid coating composition comprising micro-spheres dispersed in gelatin. Immediately after coating, the support is passed through a chill set chamber in the coating machine where the gelatin undergoes rapid gelation and the micro-spheres are immobilized.

While that invention provides a huge manufacturing advantage over then existing technologies, it needs some refinement in order to maximize its full potential value to the art. The problem is that during such machine coating and rapid gelation, the gelling agent tends to cover the surface of the micro-spheres, thereby preventing the analyte (such as DNA) from penetrating through the gel overcoat and hybridizing with probes on the surface of the micro-spheres. The gel overcoat problem was solved by using enzyme digestion as disclosed in U.S. Ser. No. 10/062,326. There is a need for a nucleic acid analysis system using such an enzyme treated coated random micro-spheres array in a whole frame imaging capture system.

SUMMARY OF THE INVENTION

According to the present invention, there is provided a solution to the problems discussed above.

The present invention overcomes the problem outlined above by enzymatically removing the gelling agent from the surface of the micro-spheres without damaging their integrity of the DNA probes on their surfaces. The enzyme treated surface maintains its physical integrity through the entire DNA hybridization process and the microarray shows a very strong hybridization signal.

The advantage is that enzyme digestion can be easily controlled to remove the required amount from the gel overcoat. Further, the enzyme, a protease, is readily available and economical to obtain.

According to a feature of the present invention, there is provided a method of identifying nucleic acid samples comprising: providing a microarray including a substrate coated with a composition including a population of nucleic acid probe modified micro-spheres immobilized in a coating containing a gelling agent or a precursor to a gelling agent, wherein a first portion of the micro-spheres is submerged in the gelatin coating and a second portion is exposed above the gelatin coating and is substantially free of gelatin, at least one sub-population of said population micro-spheres containing an optical barcode generated from at least one colorant associated with the micro-spheres and including a nucleic acid probe sequence; contacting said array with a fluorescently/chemiluminescently labeled nucleic acid sample target nucleic acid sequence; and detecting the color barcode of said sub-population of micro-spheres due to the interaction of said a fluorescently/chemiluminescently labeled nucleic acid sample probe nucleic acid sequence and said target nucleic acid sequence.

ADVANTAGEOUS EFFECT OF THE INVENTION

The invention has the following advantages.

1. Analysis of nucleic acids is simpler, less expensive, and more cost effective.
2. Nucleic acid identification systems are accurate, less complex, and less expensive.

DETAILED DESCRIPTION OF THE INVENTION

As used herein, the term "sol-to-gel transition" or "gelation" means a process by which fluid solutions or suspensions of particles form continuous three-dimensional networks that exhibit no steady state flow. This can occur in polymers by polymerization in the presence of polyfunctional monomers, by covalent cross-linking of a dissolved polymer that possesses reactive side chains and by secondary bonding, for example, hydrogen bonding, between polymer molecules in solution. Polymers such as gelatin exhibit thermal gelation that is of the latter type. The process of gelation or setting is characterized by a discontinuous rise in velocity. (See, P. I. Rose, "Theory of the Photographic Process", $4^{th}$ Edition, T. H. James ed., pages 51–67).

As used herein, the term "random distribution" means a spatial distribution of elements showing no reference or bias. Randomness can be measured in terms of compliance with that which is expected by a Poisson distribution.

As used herein, the term "enzyme" means a biological catalysts. Similar to traditional chemical catalysts, enzymes speed the rate of biological reactions by producing a transition state with a lower energy of activation than the uncatalyzed reaction. In other words, enzymes are proteins specialized for the reactions they catalyze. The preferred enzymes employed in this invention are enzymes that catalytically hydrolyze the bonds of gelatin and may be referred to as "gelatinases".

The present invention discloses a method for making an array of micro-spheres, also referred to as "beads", on a substrate wherein the surface of the micro-spheres bear capture agents, or probes, which are readily accessible to analytes with which they come in contact. The distribution or pattern of the micro-spheres on the substrate is entirely random and the micro-spheres are not attracted or held to sites that are pre-marked or predetermined on the substrate as in other methods previously disclosed. In the present invention, the micro-spheres are immobilized randomly when the gelling agent in which they are carried undergoes a sol-to-gel transition (also called "gelation").

As used herein, the term "gelling agent" means a substance that can undergo gelation as described above. Examples include materials such as gelatin, water-soluble cellulose ethers or poly (n-isopropylacrylamide) that undergo thermal gelation or substances such as poly (vinyl alcohol) that may be chemically cross-linked by a borate compound. A preferred gelling agent is alkali pretreated gelatin. Other gelling agents may by polymers that may be cross-linked by radiation such as ultraviolet radiation. Further examples of gelling agents include acacia, alginic acid, bentonite, carbomer, carboxymethylcellulose sodium, cetostearyl alcohol, colloidal silicon dioxide, ethylcellulose, gelatin, guar gum, hydroxyethylcellulose, hydroxypropyl cellulose, hydroxypropyl methylcellulose, magnesium aluminum silicate, maltodextrin, methylcellulose, polyvinyl alcohol, povidone, propylene glycol alginate, sodium alginate, sodium starch glycolate, starch, tragacanth and xanthum gum. (For further discussion on gelling agents, see accompanying reference Secundrum Artem, Vol. 4, No. 5, Lloyd V. Allen). Alpha or beta amylase or cellulase may be used to remove excess polysaccharides and agarase may be used to remove excess agar.

The invention discloses a polymeric latex bead based random microarray with each bead in the array having a distinct signature that would distinguish the bead. Such a signature may be based on color, shape or size of the bead. For signatures based on color, the color may be derived from mixing three dyes representing the primary colors R, G, B to create thousands of distinguishable beads with distinct "color addresses" (unique RGB values, e.g. R=0, G=204, B=153). The beads can be made with sites on their surfaces that are "active", meaning that at such sites physical or chemical interaction can occur readily between the bead and other molecules or compounds. Such compounds may be organic or inorganic. Usually, the molecule or compound is organic-nucleic acid and fragments thereof, are examples. As in the examples below, to the surface of each color coded bead may be attached a pre-synthesized oligonucleotide, or other biological agents. Therefore, each color address can correspond to a specific bioactive probe. These beads may be mixed in equal amounts, and the random microarray fabricated by coating the mixed beads in a single or multi-layer format. Coating methods are broadly described by Edward Cohen and Edgar B. Gutoff in Chapter 1 of "Modern Coating And Drying Technology", (Interfacial Engineering Series; v. 1), (1992), VCH Publishers Inc., New York, N.Y. For a single layer format, suitable coating methods may include dip coating, rod coating, knife coating, blade coating, air knife coating, gravure coating, forward and reverse roll coating, and slot and extrusion coating.

Coating methods are broadly described by Edward Cohen and Edgar B. Gutoff in Chapter 1 of "Modem Coating And Drying Technology", (Interfacial Engineering Series; v. 1), (1992), VCH Publishers Inc., New York, N.Y. For a single layer format, suitable coating methods may include dip coating, rod coating, knife coating, blade coating, air knife coating, gravure coating, forward and reverse roll coating, and slot and extrusion coating.

Drying methods also vary, sometimes with surprisingly varying results. Fill in your chill set and ambient drying. While the coating process described in Example 1 with low temperature chill-set in combination with high temperature drying does provide advantage of rapid manufacture, it also tends to leave the surface of micro-spheres covered with a thin layer of gelling agent. Such thin layer of gelling agent can interfere with the intended biological analysis by preventing the access of analytes to the biological probes on the surface of micro-spheres. It has been noted that if the coating was allowed to dry at ambient temperature, e.g. room temperature, after the application of gelatin melt containing micro-spheres, the upper surface of micro-spheres can be exposed without any noticeable coverage of gelling agent. However, such ambient temperature drying process takes much longer time to complete which significantly slows down the manufacture process. The present invention provides a method to resolve the problem of gel coverage over the surface of micro-spheres and the method can be easily integrated into high speed coating manufacture process.

A nucleic acid molecule is a linear polymer consisting of four bases, A, T(U), G and C (T for DNA molecule and U for RNA molecule). The interaction among four bases follows the "Watson-Crick" base pairing rule of A to T(U) and G to C mediated by hydrogen bonds. When two single strand DNA molecules having a perfect "Watson-Crick" base pairing match, they are referred as a complementary strand. The interaction between two complementary strands is termed hybridization. Sometimes complementary strands may contain one or more base-pairing mismatches as well.

In order to use a nucleic acid microarray to analyze an unknown nucleic acid sample, the nucleic acid sample to be analyzed has to be non-selectively labeled by using fluorescent dyes or chemiluminescent active molecules, followed by hybridizing the fluorescently/chemiluminescently labeled biological nucleic acid sample can be hybridized to the bead based random to the said color beads based random nucleic acid microarray. The method for labeling nucleic acid sample has been well established and the protocols for the labeling procedure can be found in many publications. The signals from both "color addressable" polymeric beads and biological sample non-selectively labeled nucleic acid fluorescence/chemiluminescence may be analyzed by a charge coupled device after image enlargement through an optical system. The recorded array image can be automatically analyzed by an image processing algorithm to obtain bioactive probe information based on the RGB color code of each bead, and the information compared to the fluorescence/chemiluminescence image to detect and quantify specific biological analyte materials in the sample. Optical or other electro-magnetic means may be applied to ascertain signature.

Although micro-spheres or particles having a substantially curvilinear shape are preferred because of ease of preparation, particles of other shape such as ellipsoidal or cubic particles may also be employed. Suitable methods for preparing the particles are emulsion polymerization as described in "Emulsion Polymerization" by I. Piirma, Academic Press, New York (1982) or by limited coalescence as described by T. H. Whitesides and D. S. Ross in J. Colloid Interface Science, vol. 169, pages 48–59, (1985). The particular polymer employed to make the particles or microspheres is a water immiscible synthetic polymer that may be colored. The preferred polymer is any amorphous water immiscible polymer. Examples of polymer types that are useful are polystyrene, poly(methyl methacrylate) or poly (butyl acrylate). Copolymers such as a copolymer of styrene and butyl acrylate may also be used. Polystyrene polymers are conveniently used. The formed micro-sphere is colored using an insoluble colorant that is a pigment or dye that is not dissolved during coating or subsequent treatment. Suitable dyes may be oil-soluble in nature. It is preferred that the dyes are non-fluorescent when incorporated in the micro-spheres.

The micro-spheres are desirably formed to have a mean diameter in the range of 1 to 50 microns; more preferably in the range of 3 to 30 microns and most preferably in the range of 5 to 20 microns. It is preferred that the concentration of micro-spheres in the coating is in the range of 100 to a million per $cm^2$, more preferably 1000 to 200,000 per $cm^2$ and most preferably 10,000 to 100,000 per $cm^2$.

The attachment of bioactive agents (often referred to as "probes") to the surface of chemically functionalized microspheres can be performed according to the published procedures in the art (Bangs Laboratories, Inc, Technote #205). Some commonly used chemical functional groups include, but not limited to, carboxyl, amino, hydroxyl, hydrazide, amide, chloromethyl, epoxy, aldehyde, etc. Examples of bioactive agents or probes include, but are not limited to, oligonucleotides, DNA and DNA fragments, PNAs, and synthetic molecules capable of interacting specifically with a target such as a nucleic acid sequence.

The enzymes used in this invention include any enzyme, enzyme preparation, or enzyme-containing formulation capable of dissolving or degrading gelatin or other gelling agent used and substantially incapable of digesting or inactivating the probe. By inactivating it is meant that the probe is inhibited from reacting with a specific target under normal conditions of reaction. Thus, "enzyme" in the context of this invention includes crude enzyme preparations, such as crude plant or bacterial fermentation broth extracts, as well as purified enzymes from plant, animal, or bacterial sources. Preparations of enzyme usable in the process are understood to include activators, cofactors, and stabilizers that are required for enzymatic activity, as well as stabilizers that enhance or preserve enzyme activity.

Examples of suitable enzymes include serine proteases such as Esperase™, Alcalase™, and Savinase™ (commercial enzyme preparations from Novo Nordisk Corporation); Multifect P-3000™, HT Proteolytic 200™, Protex 6L™ and Protease 899™ (commercial enzyme preparations from Genencor International Corporation); sulfhydryl proteases such as papain and bromelain; and metaloproteases such as Neutrase™ (a commercial bacterial metaloenzyme preparation from Novo Nordisk Corporation). The use of combinations of these enzymes and enzyme types are also envisaged under this invention. Adducts of enzymes with synthetic polymers are also envisaged in which enzyme molecules are attached to synthetic polymers, which polymers may be larger or smaller than the enzyme.

Other enzymes, preferably proteolytic, should also be suitable for this application. The use of combinations of these enzymes and enzyme types are also envisaged under this invention. Adducts of enzymes with synthetic polymers are also envisaged in which enzyme molecules are attached to synthetic polymers, which polymers may be larger or smaller than the enzyme.

Successful analytical imaging (resolution) of colored beads bearing other fluorescent or luminescent reporters is a complicated but feasible task. The preferred imaging system must be sufficiently flexible to execute all image capture tasks without the movement of the prepared sample array. Based upon its demonstrated merits, the full-frame capture of the array with a CCD camera is preferred. Carefully designed array illumination is critical to both color and fluorescent probe resolution. Considering the additional requirements imposed by luminescent resolution, the minimum optical system requirements are satisfied with a CCD sensor of at least 12-bits monochrome (<30 electrons read noise), 1 million pixels, 40% quantum efficiency, cooled (dark current <0.01 electron/sec), utilizing an f/3 lens and a magnification of approximately one. A sensor pixel approximately the size of a bead is most efficient; larger pixels compromise the spatial resolution of beads and smaller pixels compromise the signal resolution demanded for both color and reporter measurement. In theory, and in limited practice, the above requirements enable the analysis of approximately 50,000 randomly dispersed beads per field of capture. Clearly, software analysis of vast amounts of data must be implemented to manage the throughput of array images. The software analysis must provide a measure of bead reporting, localize and qualify a bead, calculate its color address, and possibly estimate its surface area in a timely manner.

A carefully designed illumination system includes well-managed epi-illumination (array illumination for the same side as the CCD camera). The illumination must be conditioned/controlled monochromatic light, sufficiently monochromatic to elicit appropriate color analysis and fluorescent excitation, and sufficiently intense to assure reasonably short exposure times (minutes). Illumination must be limited to an intensity that minimizes deleterious photolysis or heat and that assures only single-photon fluorescent processes, simplifying the effort to minimize undesirable fluorescent artifacts from solid supports and various biological materials essential to the arrays. The full-frame image-capture capability of the appropriately implemented CCD camera is uniquely qualified to adhere to the requirements imposed by feasible illumination systems, but must be assisted by precise optical filters to analyze light for the purpose of discerning color and fluorescence. Appropriate interference filters are readily designed upon specifying color dye and fluorescent reporter characteristics. Further, the specified CCD camera can accommodate the capture and analysis of luminescent reporters in about a 10 minute time period per field of capture. A tethered desktop computer appropriately linked to hardware can feasibly implement all analyses within a time period commensurate with the minutes required to gather all relevant array data.

While the above hardware specifications may feasibly manage the analysis of random bead arrays, the analysis is feasible only if the supporting materials are optically qualified. Optical requirements of the array support include appropriate cleanliness (artifact free, e.g., dust, debris, digs, scratches and inclusions) and physical/optical requirements that minimize fluorescent quenching, preclude fluorescent supports or colored dyes, and present a spatial noise frequency and amplitude that minimally interfere with the array analysis. In addition, the appropriate optical coupling of the array to the imaging system must accommodate the requirements of both illumination and capture.

That the entire process is feasible may be assumed on the basis that "common" photographic film is coated and processed to produce images that resolve millions of colors at a spatial resolution of a few micrometers. By comparison, the task of analyzing the random-bead microarray seems modest in that only a thousand colors of about 10-micrometer resolution is required. However, the bit-depth/sensitivity required, the essential delicate biochemistries and the control of fluorescence present many challenges, and much of the resolution common to photographic film will be sacrificed for the sake of meeting the developmental challenges implicit in array analysis.

Figure 2:
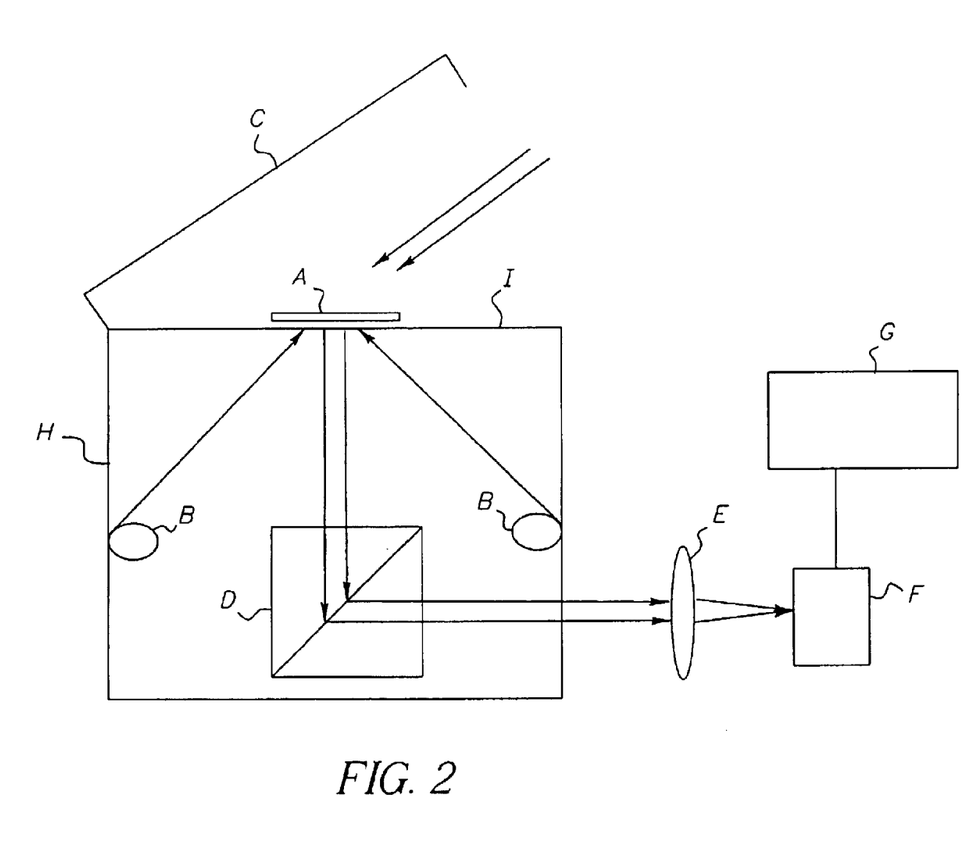
FIG. 2 is a schematic diagram illustrating the gelatin coated micro-sphere based nucleic acid detection system comprising instrumentation and appropriate control units.

One of the feasible system set up for nucleic acid analysis based on the description above was schematically shown in FIG. 2 with the inventive color beads based nucleic acid microarray and the necessary hardware components. The design principle for such a system is described in detail in Example 5. However, one skilled in the art can modified the system to produce other variations similar to what is described in this invention. As shown coated microarray A was placed on the surface of closed box H containing light source B and light deflector D. The surface I contacting A can be made of transparent glass or other plastic materials. E is an optical lens to focus a light signal from A onto full frame electronic detector F (e.g., CCD, MOS), and the signal was analyzed by computer G. In practice, the color beads barcode information can be captured by illuminating the microarray with a conditioned/controlled monochromatic light B. If the reporter signal from A is due to fluorescence, the fluorescence can be excited using selected monochromatic light from B with cover C closed. If the reporter signal from A is chemiluminescence, the microarray A will be in contact with a chemiluminescence substrate solution and the reporter signal can be captured in the dark with cover C closed.

Figure 3:
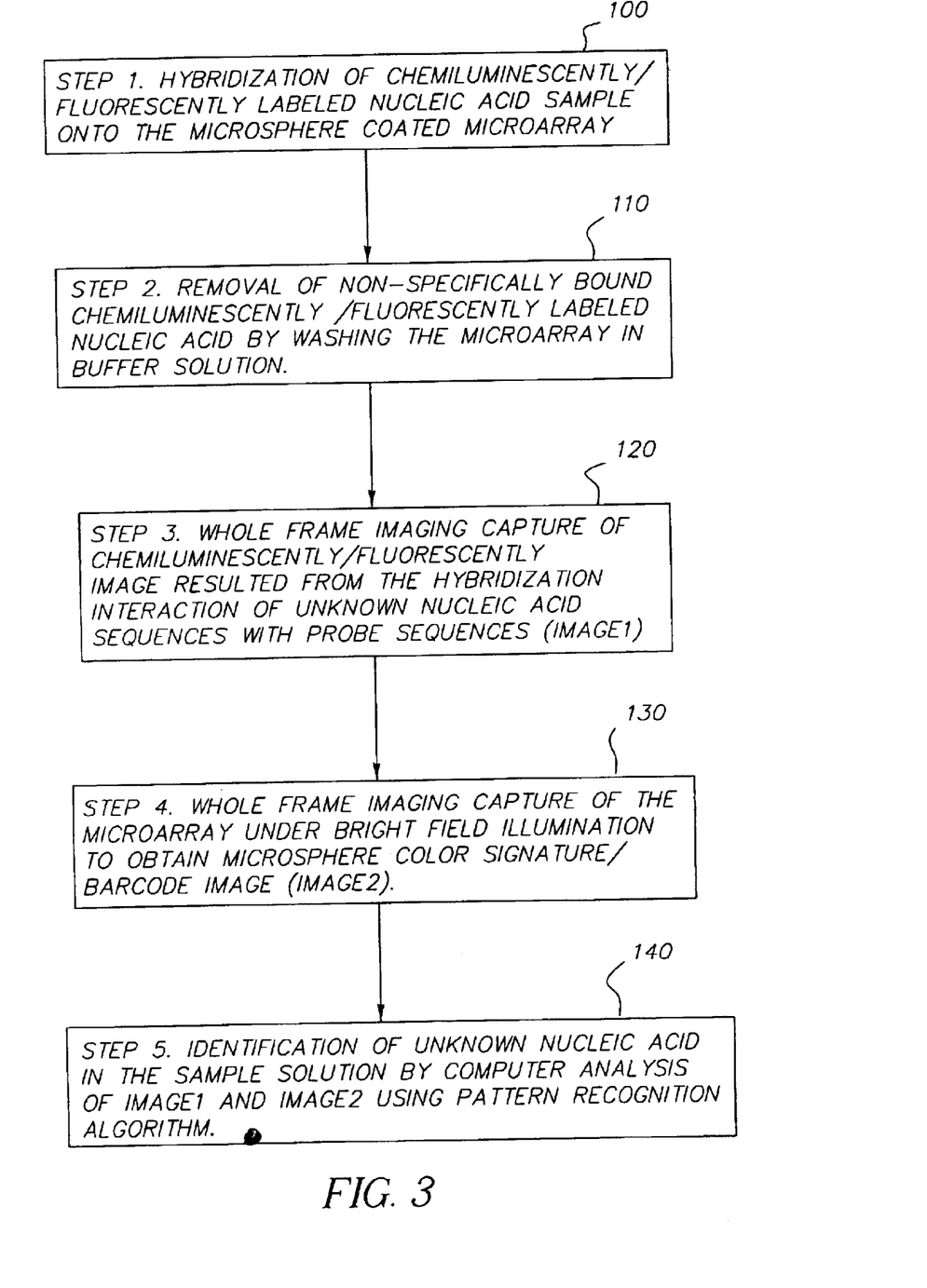
FIG. 3 is a workflow chart showing the process of how to use the microarray system to analyze an unknown nucleic acid sample.

FIG. 3 shows schematically a workflow chart on how to use the described nucleic acid analysis system. In step 1, box 100 fluorescently/chemiluminescently labeled nucleic acid sample is hybridized to the beads based random microarray. This step requires good physical contact of the coated microarray with the nucleic acid sample by either placing a layer of sample solution on the coated side of the microarray or dipping the microarray into the sample solution. The non-specific bound nucleic acid will be removed in step 2 box 110 through multiple washing of the microarray in buffer solution. In step 3, box 120, the fluorescence/chemiluminescence signals which resulted from the hybridization of the unknown nucleic acid sample with probe sequences on the surface of the coated micro-spheres are analyzed by an imaging system, as shown in FIG. 2. The recorded fluorescence/chemiluminescence image designated as IMAGE1 stored in computer G. In step 4 box 130, a bright field illumination condition is used to capture the color beads image to obtain the optical signature/barcode information of the coated microarray. This image will be designated as IMAGE2 and stored in computer H. In the final step, both IMAGE1 and IMAGE2 can be automatically analyzed using an image processing algorithm to identify the unknown nucleic acid sequences by comparing IMAGE1 with IMAGE2.

EXAMPLES

Example 1

This example illustrates the preparation of colored micro-spheres by incorporating dyes into the micro-spheres and the process of preparing the coating containing colored micro-spheres.

Twenty four grams of a 4% aqueous suspension of polystyrene beads prepared by emulsion polymerization and having a mean size of 9.5 micrometers was combined with 0.48 grams of poly(vinyl alcohol)(75% hydrolyzed, molecular weight 2000).

A suspension of magenta colored beads was prepared by first dissolving 0.084 grams of Dye 1 in 0.08 grams of toluene and 7.92 grams of acetone. From the above suspension of polystyrene beads containing poly(vinyl alcohol) an amount of 8.16 grams was then added slowly (drop-wise) to this solution of the dyes while stirring to prepare a suspension of colored beads. The suspension of colored beads was then filtered using a porous cotton filter, poured into a dialysis bag (12,000 to 14,000 molecular weight cut off) and washed with distilled water for one hour. After washing, the suspension of colored beads was filtered again using a porous cotton filter. The concentration of magenta colored beads in the suspension after this final step was 1.2%.

Suspensions of cyan and orange colored beads were prepared in a similar manner using Dye 2 and Dye 3 (Sudan Orange 220 from BASF corporation) respectively in place of Dye 1. The concentration of colored beads in these suspensions were 1.6% and 1.45% respectively.

Formulations for coating were prepared in the following manner.

Formulation 1 (invention):

This was prepared by combining 4.0 grams of the suspension of cyan colored beads, 5.33 grams of the magenta colored beads and 4.41 grams of the orange colored beads with 13.91 grams of a 11.5% solution of lime processed ossein gelatin in water, 3.2 grams of coating aid (6.8% solution of Triton X 200E in water) and 49.15 grams of distilled water.

Formulation 2 (Control):

A second formulation for coating was prepared by combining the same amounts cyan, magenta and orange colored beads with 7.27 grams of poly(vinyl alcohol) (GH23 from Nippon Gohsei) and 55.79 grams of water. The amount of coating aid was the same as in formulation 1. The amount of poly(vinyl alcohol) was chosen to match the viscosity of formulation 1 at the higher temperatures (See, below).

Both samples (formulation 1 and formulation 2) were equilibrated in a 50° C. water bath for 30 minutes and then analyzed using a Rheometric Fluid Rheometer. Viscosities were determined as a function of temperature by the dynamic oscillatory technique as the samples were cooled at the rate of one degree centigrade per minute.

TABLE #1

| Temperature (° C.) | Viscosity (centipoise) | |
| --- | --- | --- |
| | Formulation 1 | Formulation 2 |
| 45 | 2.0 | 2.0 |
| 40 | 2.2 | 2.2 |
| 35 | 2.8 | 2.9 |
| 30 | 3.4 | 3.5 |
| 25 | 5.1 | 4.3 |
| 20 | 2107 | 4.6 |
| 15 | 100,000 | 6.0 |
| 10 | 440,000 | 7.9 |

It may be seen from the above data that at the higher temperatures (above about 30° C.), both samples behave similarly in terms of the increase in viscosity upon cooling. However, below about 25° C. formulation 1 (invention) displays a much more dramatic increase in viscosity because of gelation. Such behavior is not exhibited by formulation 2 (control). The viscosity of formulation 1 increases by several orders of magnitude as the temperature is reduced from 25° C. to 10° C. The temperature of onset of gelation is estimated to be 21.8° C.

A suspension of Cyan colored beads was prepared by first dissolving 0.001 grams of dye 2 in 0.05 grams toluene and 4.95 grams acetone. 2.5 grams of a 4% aqueous suspension of polystyrene beads prepared by emulsion polymerization and having a mean size of 9.5 micrometers was then added slowly (drop-wise) to this solution of the dyes while stirring to prepare a suspension of 11% dye loaded cyan dye. The suspension of colored beads was then filtered using a porous cotton filter, poured into a dialysis bag (12,000 to 14,000 molecular weight cut off) and washed with distilled water for one hour. The concentration of cyan beads in the suspension after this final step was 0.78%.

Suspensions of the other 5 levels of cyan dye incorporated into the beads were prepared in a similar manner using 0.002 grams dye 2, 0.006 grams dye 2, 0.007 grams dye 2, 0.009 grams dye 2, and 0.01 grams dye 2.

For preparing the last two samples, 2.5 grams of a 4% aqueous suspension of polystyrene beads prepared by emulsion polymerization and having a mean size of 9.5 micrometers was combined with 0.48 grams of poly(vinyl alcohol)

Example 2

This example illustrates the attachment of pre-synthesized single strand oligonucleotide probe to the surface of dye incorporated beads.

Three DNA oligonucleotide probe sequences and their complementary target sequences were used. The probe sequence was modified with primary amine at their 5 prime end and the target sequence was modified with biotin at their 5 prime end.

| yed Microsphere | Probe Sequence | Complementary Target Sequence |
|---|---|---|
| ye 1 | 5'-amino modification-<br>AGGTGAACGTGGATGAAGTT-3' | 5'-biotin modification-<br>AACTTCATCCACGTTCACCT-3' |
| ye 2 | 5'-amino modification-<br>TGGGTTCTCTTGGCTGTTACTG-3' | 5'-biotin modification-<br>CAGTAACAGCCAAGAGAACCCA-3' |
| ye 3 | 5'-amino modification-<br>AAGCTGTTAGCCGAGTAGCG-3' | 5'-biotin modification-<br>CGCTACTCGGCTAACAGCTT-3' |

(75% hydrolyzed, molecular weight 2000). This was used in place of the polystyrene beads alone.

A 4% aqueous suspension of 2.5 grams polystyrene beads prepared by emulsion polymerization and having a mean size of 9.5 micrometers was combined with 0.48 grams of poly(vinyl alcohol)(75% hydrolyzed, molecular weight 2000).

A suspension of Magenta colored beads was prepared by first dissolving 0.01 grams of dye 1 in 0.05 grams of toluene and 4.95 grams acetone. From the above suspension of polystyrene beads containing poly(vinyl alcohol) an amount of 5.00 grams was then added slowly (drop-wise) to this solution of the dyes while stirring to prepare a suspension of 5% dye loaded Magenta dye. The suspension of colored beads was then filtered using a porous cotton filter, poured into a dialysis bag (12,000 to 14,000 molecular weight cut off) and washed with distilled water for one hour. The concentration of cyan beads in the suspension after this final step was 2.59%.

Suspensions of the other 4 colors of dye incorporated into the beads were prepared in a similar manner using 0.05 grams of each of the following dyes: dye 2(114FN-D89), dye 3 (BASF Sudan Orange 220), dye 4 (MM2500FAN), and dye 5 (BASF Yellow 075). Plain polystyrene beads were also used at 4% for the color white.

Figure 1:
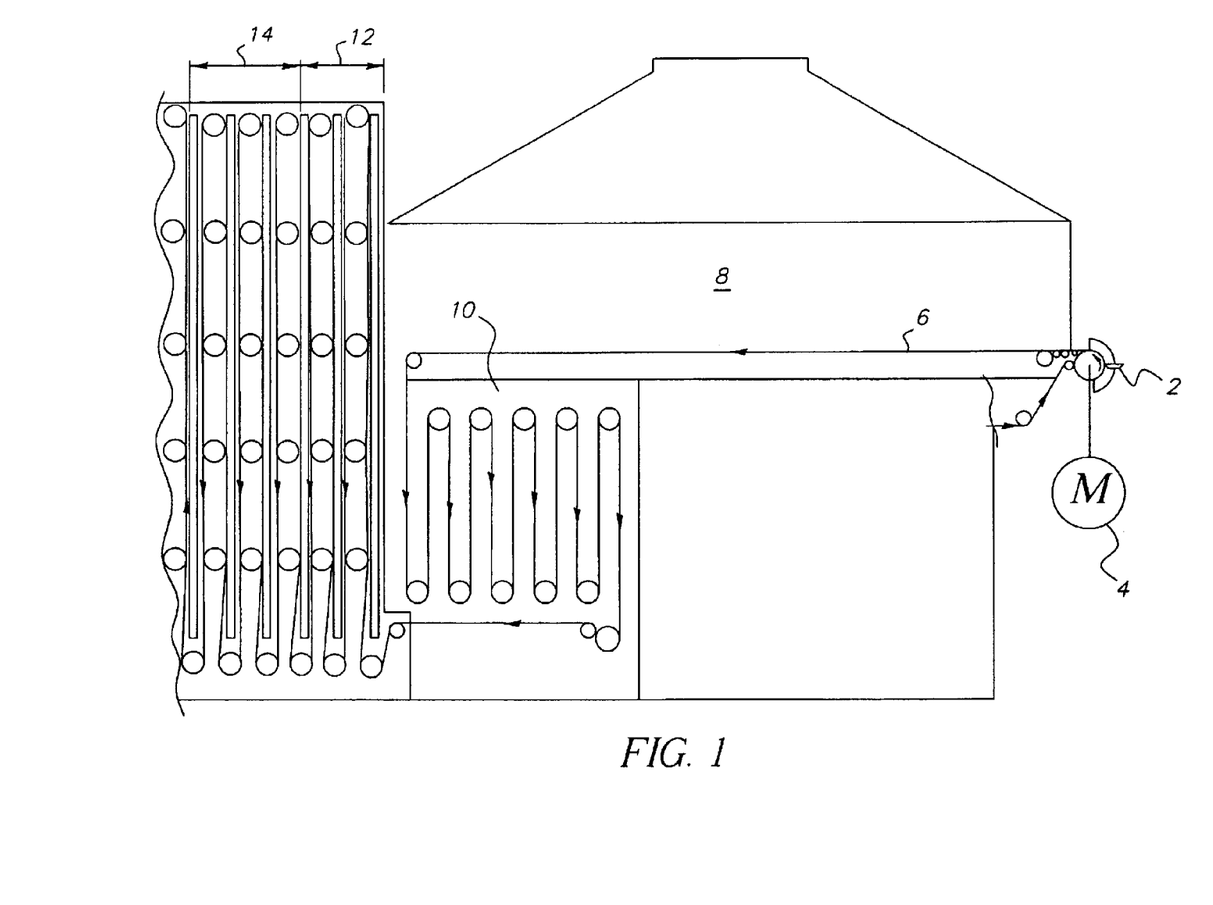
FIG. 1 is a diagram of a coating device.

Formulation 1 and formulation 2 from Example 1 were coated on a 0.18 mm thick substrate of polyethyleneterephthalate (PET) containing 6% by weight titanium dioxide using the coating device shown in FIG. 1. The formulations were introduced through a slot coating die 2, driven by a motor M 4, at a temperature of 45° C., on to a 12.7 cm wide web 6 moving at the rate of 3.7 m/min. The flow rate was adjusted to provide a level of 0.043 g/m² for each of the cyan, magenta and orange colored beads. The coatings were chill-set in a 2.4 m long chilling section 8 that was maintained at a temperature of 4° C. and 56.6% RH and then passed through a conditioning chamber 10 before being dried in a first 12 and then a second 14 drying section that were 9.8 m and 11.6 m in length respectively. The first drying section 12 was maintained at a temperature of 21° C. and 33.2% RH and the second 14 was maintained at a temperature of 37.8° C. and 18.6% RH.

One hundred microliters of Dye incorporated beads (4% w/v) was rinsed three times in acetate buffer (0.01 M, pH 5.0), and combined with one hundred microliters of 20 mM 2-(4-Dimethylcarbomoyl-pyridino)-ethane-1-sulfonate and ten percent of polyethyleneinine. The mixture was agitated at room temperature for one hour and rinsed three times with sodium boric buffer (0.05 M, pH 8.3). The beads were re-suspended in sodium boric buffer.

An oligonucleotide DNA probe with 5'-amino-C6 modification was dissolved in one hundred microliters of sodium boric buffer to a final concentration of 40 nmol. A 20 microliters of cyanuric chloride in acetonitrile was added to the DNA probe solution and the total volume was brought up to 250 microliter using sodium boric buffer. The solution was agitated at room temperature for one hour and then dialyzed against one liter of boric buffer at room temperature for three hours.

A 100 microliters of the dialyzed DNA solution was mixed with 200 microliters of beads suspension. The mixture was agitated at room temperature for one hour and rinsed three times with sodium phosphate buffer (0.01 M, pH 7.0). The modified beads were coated onto transparent plastic support according to formulation 1 as described in Example 1.

Example 3

This example illustrates the hybridization and detection of target nucleic acid sequences to the gelatin coated microsphere based microarray.

An oligonucleotide DNA with 5'-biotin labeling, which has complementary sequence to the DNA probe, was dissolved in a hybridization solution containing 0.9 M NaCl, 0.06 M $NaH_2PO_4$, 0.006 M EDTA, and 0.1% SDS, pH 7.6 (6×SSPE-SDS) to a final concentration of 1 μM. The bead coated microarray was hybridized in the hybridization solution starting at 68° C. and slowly cooled down to room temperature. Following hybridization, the microarray was washed in 0.5×SSPE-SDS for 15 minutes three times. The microarray was incubated in a solution containing streptavidin-horseradish peroxidase conjugate in a 0.01 M phosphate buffer 0.1 M NaCl pH 7.0 for 1 hour at room temperature. Following the incubation, the microarray was rinsed three times with the incubation buffer.

The hybridization completed microarray was imaged with white light illumination using Olympus BH-2 microscope (Diagnostic Instruments, Inc. SPOT camera, CCD resolution of 1315×1033 pixels) to obtain the color beads barcode signature information, followed by a dark field chemiluminescence image capture by placing a thin layer of SuperSignal® ELISA chemiluminescence substrate solution (purchased from PIERCE ENDOGEN) over the microarray.

Example 4

This example illustrates the influence of the enzyme digestion on DNA hybridization onto coatings containing colored micro-spheres or beads.

Figure 4A:
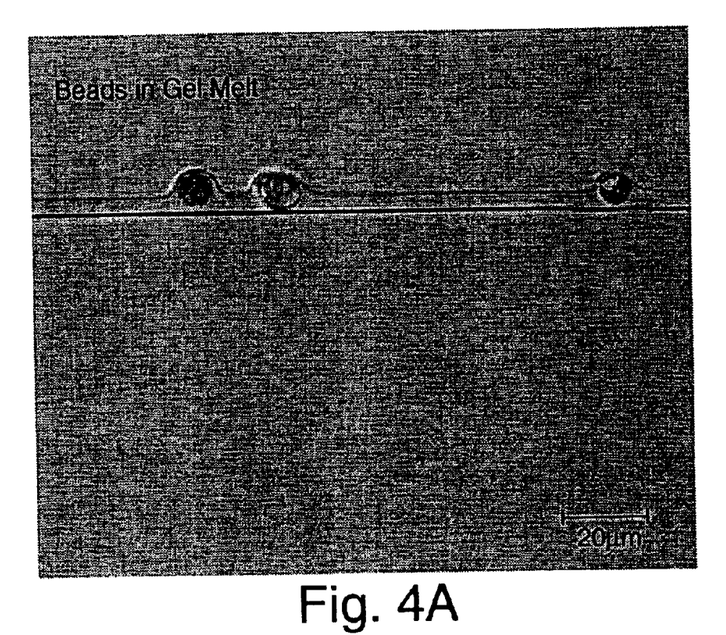
FIGS. 4A, 4B, 4C and 4D show cross sections of a microarray treated with gelatinase for different periods: 0 minutes–4B; 5 minutes–4C; and 7 minutes–4D.
Figure 4B:
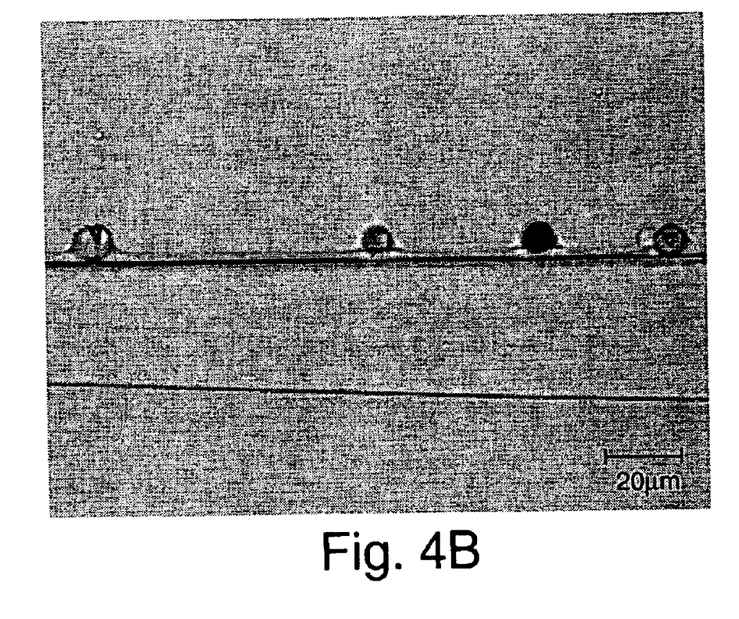
Figure 4C:
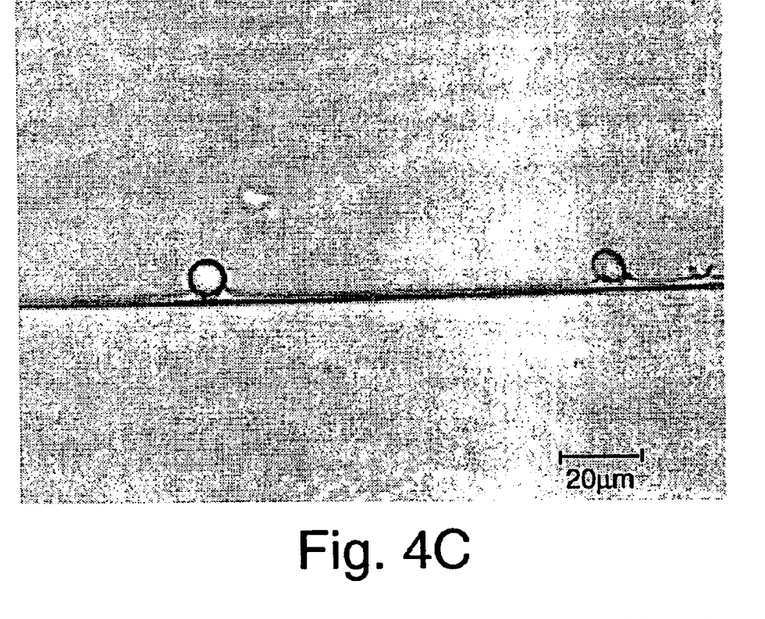
Figure 4D:
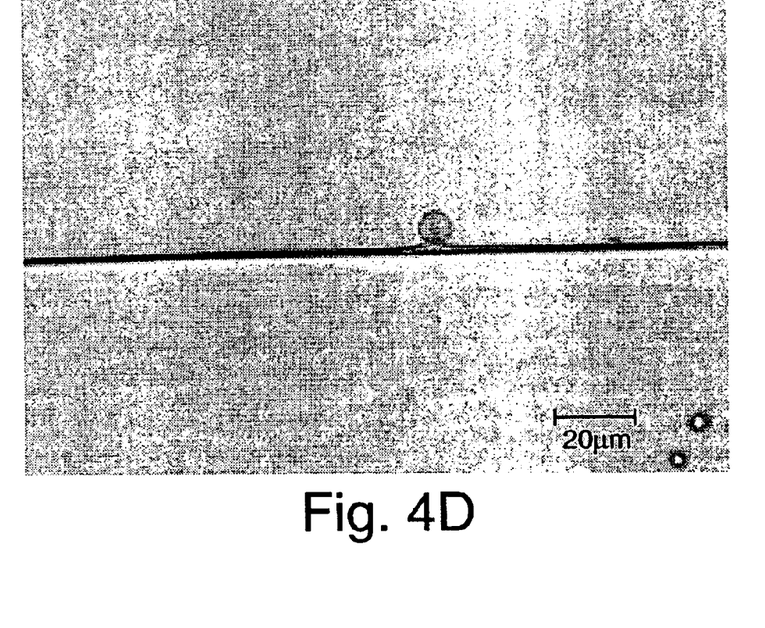

Gelatinase was purchased from Genencor International Inc. and was used without further purification. Galatinase of 0.5 g was dissolved in 60 mL of water. Coating containing colored micro-spheres was immersed in the enzyme solution for various length of time at 37° C. and the enzymolysis reaction was stopped by dipping the enzyme treated coating into a running water bath for 5 minutes. The coatings treated with gelatinase for 0, 3, 5, and 7 minutes were cross sectioned and the cross sections were imaged under microscope to visualize the extent of gelatin removal. FIG. 4A shows treatment after 0 minutes; FIG. 4B shows treatment after 3 minutes; FIG. 4C shows treatment after 5 minutes; and FIG. 4D shows treatment after 7 minutes. It will be observed that as the time for treatment increases, a larger surface of the bead is exposed. The biotin labeled target DNA fragment complimentary to the probe DNA sequence on the surface of the beads were hybridized to the coating treated with gelatinase for various length of time. The chemiluminescence signal was detected as described in Example 3 and the results were summarized in Table 2

TABLE 2

| Time of Gelatinase treatment | 0 minutes | 3 minutes | 5 minutes | 7 minutes |
|---|---|---|---|---|
| Chemiluminescence detection | No | Yes | Yes | Yes |

Figure 5A:
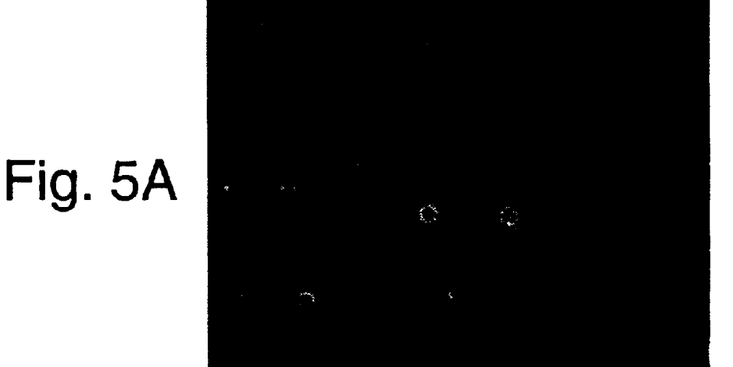
FIGS. 5A, 5B, and 5C show coated DNA microarrays captured under a dark field without illumination after exposure to a solution containing target nucleic acid sequence.
Figure 5B:
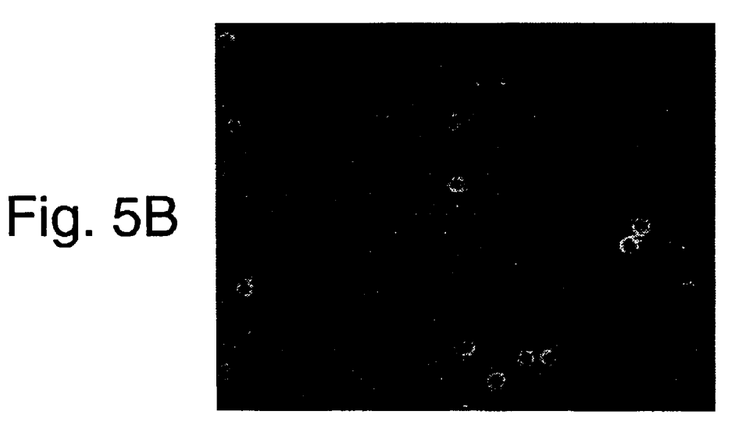
Figure 5C:
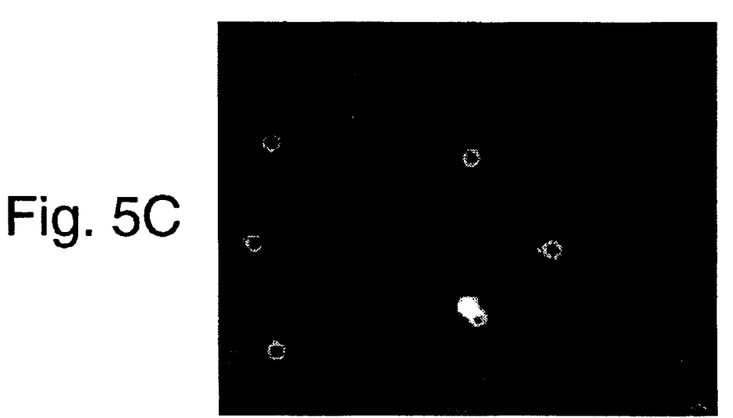

The chemiluminescence images for 3, 5 and 7 minutes enzyme treatment are shown respectively in FIGS. 5A, 5B, and 5C. It is important that the detected micro-sphere signal improves as more micro-sphere surface is exposed.

This example illustrates only one condition for the enzymolysis reaction. However, the condition for the enzymolysis reaction can also be performed by dissolving the enzyme in buffered solutions or organic solvents and carried out at appropriate temperature. One skilled in the arts can modify the process to accommodate certain desirable applications.

Any method of enzymolysis is within the scope of the present invention provided the gelling agent is substantially removed from the surface of the micro-sphere which means that the probe attached to the surface is sufficiently free of gelatin to interact with the intended target.

Example 5

This example illustrates the preferred design principle to image and analyze coated color beads on a flat surface.

The most accommodating approach to obtain image data from a reporting flat object is full-frame image capture. The most important physical aspects of the image capture system is the balance between efficient light collection, optical resolution and effective illumination of the object and the balanced system must accommodate luminescent, fluorescent and absorbance modes of optical reporting. Further, the system must do so without significant movement of the object of interest and the imaging data must support the necessary measures relating to subsequent analysis. The design solutions to many of these requirements are well known to practitioners of the art; however, the system design to accommodate all requirements into a single practical solution requires invention.

A rational approach to design is to adhere to the most important dictates of the modes of imaging/detection: luminescent, fluorescent and absorbance. The design principles are illustrated in FIGS. 6A, 6B and 6C.

Figure 6A:
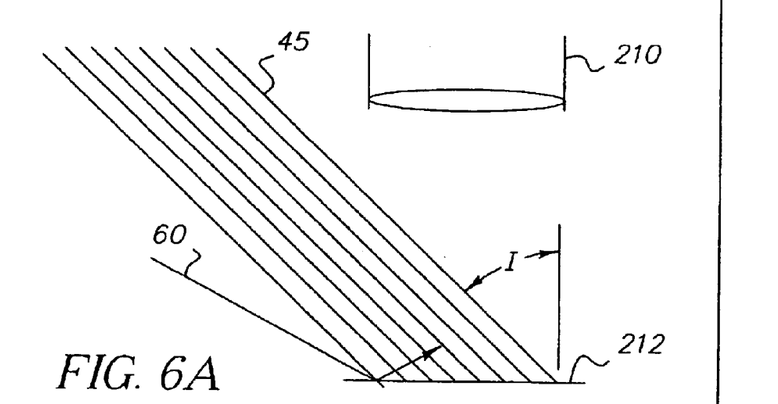
FIGS. 6A, 6B, and 6C schematically show the optical design principle respectively used to analyze coated color beads signals in absorption, fluorescence and chemiluminescence detection systems.
Figure 6B:
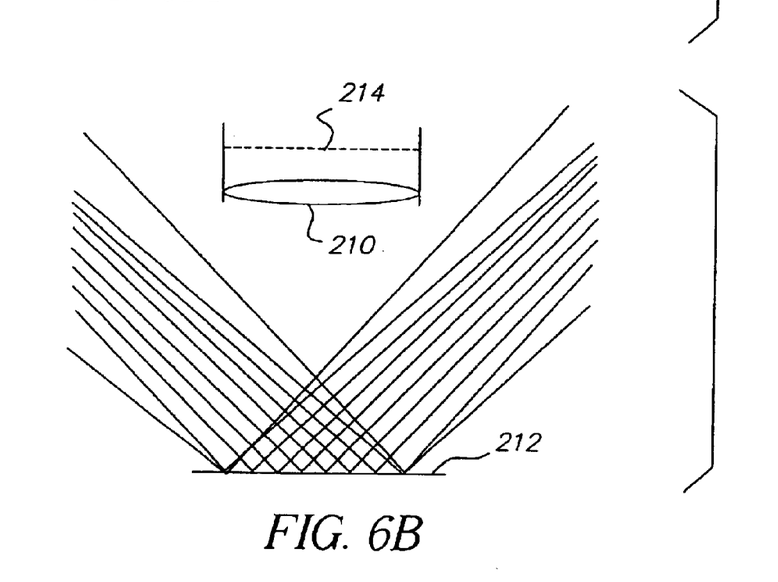
Figure 6C:
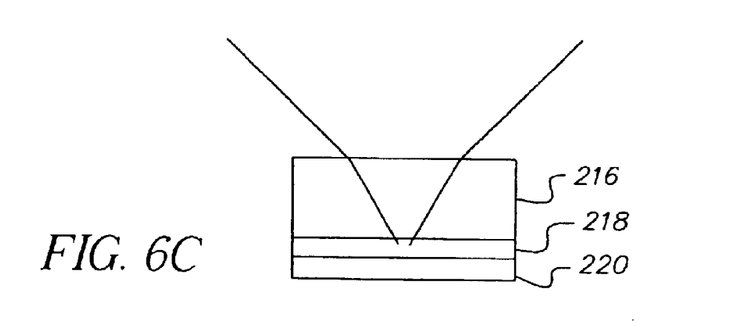

FIG. 6A shows a lens 210 and object plane 212. FIG. 6B shows lens 210, object plane 212, and filter 214. FIG. 6C shows optical platen 216, aqueous layer 218, and object 220 on a mirror support.

The chief requirement of luminescent imaging/detection is efficient light detection, influenced by both collection and photometric integration. Efficient light collection requires a lens of large numerical aperture whose diameter is approximately the size of the field of view and positioned at a working distance that is close to the object. Practical solutions and cost lead to the solution illustrated in FIG. 6A, wherein an optical system specification of a lens 210 approximately f2 (lens diameter about half the working distance between lens 210 and object plane 212) is represented. Photometric integration requires a well-implemented sensor having sufficient dynamic range to generate a signal/noise ratio appropriate to support analysis. In practice, an integrated, cooled CCD sensor of 12-bits resolution and a quantum efficiency of >40% that produces a signal/noise ratio >3000 suffices for contemporary chemiluminescent image capture and readily enables photometric analysis with a linear dynamic range of measure. An important practical limitation imposed by a lens with high numerical aperture is a small depth of focus that requires controlled flatness of the object plane. The plane of the object is consequently restricted in this system design by an optical platen (see FIG. 6C). Further, the reporting surface of the object is necessarily wet which offers the opportunity to optically couple the sample to the optical platen. Optically coupling the object to the system is essential to the intrascenic dynamic range of the measure (minimizing haze and other optical artifacts that detract from measuring bright and dim features within the same field of view).

The chief requirements of fluorescent imaging/detection are both efficient light detection and appropriate management of illumination. The design of efficient light detection discussed above (including optical coupling) delivers all of the essential capability to fluorescent imaging. Illumination management requires that excitation and emission light be discriminated. Design considerations for conditioning the wavelength of excitation light is discussed below (addressing absorption). Implicit to appropriate illumination management is the elimination of stray light, particularly that which emanates from materials that may fluoresce. Central to the design solution of this system is the minimization of excitation light from the productive path of emitted light (the acceptance cone of the lens system), as shown in FIG. 6A. This method of exciting fluorescence is traditionally recognized by those familiar with the art to be most effective; the method is generally called epi-illumination. Ideal epi-illumination of a flat surface (object plane) would involve illumination with parallel light at a 45° angle of incidence (shown as "I" in FIG. 6A). In practice, an angle of incidence substantially less than 45° increases the possibility that excitation light from a normal reflection will enter the acceptance cone of the lens; sources of normal reflection include stray light from illumination and features in the field of view that deviate from the object plane. An example of a design using a small angle of incidence is that which uses "ring-light" illumination. Another constraint is that the angle of incidence must be less than about 60°, else an increasing amount of excitation light will not interact with the sample due to the total reflection caused by the critical angle of the platen (FIG. 6C). Any practical system of illumination will include light that is not parallel. It is practical, indeed usual, to illuminate with light that is divergent as illustrated in FIG. 6B, where the illumination is shown as the finer lines entering from both sides of the object, a common method of epi-illumination used to enhance illumination uniformity. The illustration depicts slightly divergent light (about 18 degrees, or approximately f11), much less divergent than many commonly used methods such fiber illumination. The epi-illumination shown in FIG. 6B is preferred, since the extreme angles of incidence (and reflectance shown as bold lines) minimize the possibility of stray light entering the acceptance cone of the lens or critically reflecting from a planar surface.

A further important system design solution is embodied in FIG. 6C. The platen composition is a controlled optical surface, and as such may be constructed to minimize haze, autofluorescence and reflectance. Note that in this system design, the platen is the only material with which the excitation light has the opportunity to interact. Preferred composition of the platen is optical acrylic (UV transparent), whose sensor/illumination side is coated with an anti-reflective layer, and whose sample/object side is coated with an anti-abrasion layer (hard-coat). Other compositions (such as fused silica) are acceptable, but will manifest some performance decrement (transmit less light). As described above, the aqueous layer (ubiquitous to biological/biochemical systems) optically couples the sample surface to the platen and the object (the bead monolayer) is coated onto a flexible support having a mirror surface. The vast majority of the excitation light, which does not interact with the object beads, is simply reflected out of the system, away from the lens.

To summarize, in this preferred epi-illumination system for fluorescent excitation, the excitation light interacts only with a controlled optical component, a thin aqueous solution and a target bead before the light has a significant probability of entering the acceptance cone of the lens. Consequently, the lens system need only discriminate excitation from emitted light that emanates from the target bead. The discrimination of excitation from emitted light is commonly practiced in fluorescent imaging/detection, commonly using an interference filter (see filter 214-FIG. 6B). Such filters can be very costly and the capability of the filter to efficiently discriminate excitation and emitted light is often the chief limitation of detection sensitivity. In this preferred system design, the requirement of the filter to discriminate is reduced approximately 1000-fold compared to many fluorescent detection systems.

The chief requirements of absorption imaging/detection (generally called colorimetry) involve spectral resolution and photometry. The photometric precision of the system described above is more than 10-fold better than the basic system requirements for resolving thousands of "colors". The application requirement is similar to resolving/deconvoluting R, G, B and combinations/levels thereof. The fundamental method of color resolution involves measurement of the relative absorption characteristics of an object with differing wavelengths of light; the relative differences are tabulated to functionally define categories of dye combinations and levels. The dyes chosen must not interfere with other reporting optical elements, such as fluorochromes. One way to minimize anticipated interference is to choose "color" dyes whose absorbance spectrum is higher than any excitation/emission spectrum of the reporting fluorochromes.

Given a sufficient photometric precision, the number of colors that may be resolved (functionally defined) will depend upon the management of illumination and detection of light. Two fundamentally different methods of light management for the purpose of color resolution are either spectrally resolving "white" light before or after the light interacts with an object. The above system design requires that both methods be invoked for the sake of fluorescent imaging. The preferred design solution that is suitable for both absorption and fluorescent modes of imaging detection is to manage the spectral resolution of the illumination. Therefore, the illumination is managed by a light source and monochrometer, having sufficient power and resolution to accommodate both modes of imaging. The solution is cost effective because the multi-filter design and implementation that would accommodate the excitation of multiple fluorescent probes and absorption of multiple colored dyes would easily exceed the cost of monochromator. Since the spectral excitation/absorption of the organic fluorochromes and dyes are relatively broad, a spectral resolution of only about 20 nm will suffice and the delivered illumination energy will be correspondingly higher than that associated with a "high resolution" monochromater (typically <2 nm). That the delivered energy will suffice for fluorescent imaging is assured by the sensitivity of the camera which is designed for luminescent imaging.

The invention has been described in detail with particular reference to certain preferred embodiments thereof, but it will be understood that variations and modifications can be effected within the spirit and scope of the invention.

PARTS LIST 2 coating die
4 motor
6 web
8 chilling section
10 conditioning chamber
12,14 drying section
100 fluorescently/chemiluminescently labeled nucleic acid sample hybridized to the beads based random microarray
110 non-specific bound nucleic acid removed through multiple washing
120 fluorescently/chemiluminescently signals analyzed
130 bright field illumination condition used to capture color beads image to obtain optical signature/barcode information of coated microarray
140 IMAGE1 and IMAGE2 automatically analyzed using image processing algorithm to identify unknown nucleic acid sequences
210 lens
212 object plane
214 filter
216 optical platen
218 aqueous layer
220 object

What is claimed is:
1. A method of identifying biological samples comprising:
providing a micro-array including a substrate coated with a composition including a population of biological probe modified micro-spheres immobilized in a coating containing a gelling agent, at least one sub-population of said population of micro-spheres containing an optical barcode generated from at least one colorant associated with the micro-spheres and including a biological probe sequence;

enzymatically removing a portion of the gelling agent over the micro-spheres such that a first portion of the micro-spheres is submerged in the gelling agent and a second portion is exposed above the gelling agent and is substantially free of gelling agent;

contacting said array with a biological sample labeled with one of a fluorescent or chemiluminescent label target; and detecting the optical barcode of said sub-population of micro-spheres due to the interaction of said biological probe and said labeled biological sample target; and identifying the biological sample from said detected optical bar code.

2. The method of claim 1 wherein said micro-array population of micro-spheres includes a plurality of sub-populations of micro-spheres, wherein each said sub-population of micro-spheres obtains a unique optical barcode and has a unique probe.

3. The method of claim 1 wherein said optical barcode is generated by two or more colorants.

4. The method of claim 1 wherein said optical barcode is generated by a mixture of red (R), green (G), and blue (B) colorants.

5. The method of claim 1 wherein said at least one sub-population of micro-spheres has a luminescent property to produce a luminescent image and wherein said detecting includes:
(a) whole frame imaging capture of the luminescent image resulting from said interaction of said biological probe and said labeled biological sample target to produce a first image;
(b) whole frame imaging capture of said microarray under bright field illumination to obtain micro-sphere color signature/barcode image to produce a second image; and
(c) processing said first and second images to obtain identification of said biological sample.

6. The method of claim 5 wherein said processing uses a pattern recognition algorithm to obtain said identification.

7. The method of claim 1 wherein said at least one sub-population of micro-spheres has a fluorescent property and wherein said detecting includes:
(a) whole frame imaging capture of the fluorescent image resulting from said interaction of said biological probe and said fluorescently or chemiluminescently labeled biological sample target to produce a first image;
(b) whole frame imaging capture of said micro-array under bright field illumination to obtain micro-sphere color signature/barcode image to produce a second image; and
(c) processing said first and second images to obtain identification of said biological sample.

8. The method of claim 1 wherein said substrate is characterized by an absence of specific sites capable of interacting physically or chemically with the micro-spheres.

9. The method of claim 1 wherein said micro-spheres bear surface active sites which contain said probe.

10. The method of claim 1 wherein said micro-spheres have a mean diameter between 1 and 50 microns.

11. The method of claim 1 wherein said micro-spheres have a mean diameter between 3 and 30 microns.

12. The method of claim 1 wherein said micro-spheres have a mean diameter between 5 and 20 microns.

13. The method of claim 1 wherein said micro-spheres in the composition are immobilized on the substrate in a concentration between 100 and 1 million micro-spheres per $cm^2$.

14. The method of claim 1 wherein said micro-spheres in the composition are immobilized on the substrate in a concentration between 1000 and 200,000 micro-spheres per $cm^2$.

15. The method of claim 1 wherein said micro-spheres in the composition are immobilized on the substrate in a concentration between 10,000 and 100,000 micro-spheres per $cm^2$.

16. The method of claim 1 wherein said micro-spheres comprise a synthetic or natural polymeric material.

17. The method of claim 16 wherein said polymeric material is an amorphous polymer.

18. The method of claim 17 wherein said amorphous polymer is polystyrene.

19. The method of claim 1 wherein said micro-spheres contain a polymeric material and less than 30 weight percent of a crosslinking agent.

20. The method of claim 1 wherein said micro-spheres have the property of being prepared by emulsion polymerization or limited coalescence.

21. A method of identifying biological samples comprising:
providing a microarray including a substrate free of receptors designed to physically or chemically interact with microspheres, said substrate coated with a composition including a population of micro-spheres immobilized at random positions on the substrate, at least one sub-population of said population of micro-spheres containing an optical bar code generated from at least one colorant associated with the micro-spheres, having one of a luminescent or fluorescent property and including a biological probe;

contacting said microarray with a biological sample target having a corresponding luminescent or fluorescent property; and detecting the optical bar code of said sub-population of micro-spheres due to the interaction of said biological probe and said biological sample target to produce a corresponding luminescent or fluorescent image;

(a) whole frame imaging of the luminescent or fluorescent image resulting from said interaction to produce a first image;
(b) whole frame imaging capture of said microarray under bright field illumination to obtain micro-sphere color signature/barcode image to produce a second image; and
(c) processing said first and second images to obtain identification of said identification of said biological sample.

22. The method of claim 21 wherein said processing uses a pattern recognition algorithm to obtain said identification.

23. The method of claim 21 wherein said microarray population of micro-spheres includes a plurality of sub-populations of micro-spheres, wherein each said sub-population of micro-spheres contains a unique optical barcode and has a unique biological probe.

24. The method of claim 21 wherein said optical barcode is generated by two or more colorants.

25. The method of claim 21 wherein said optical barcode is generated by a mixture of red (R), green (G), and blue (B) colorants.

* * * * *